United States Patent [19]

Kuo et al.

[11] Patent Number: 5,504,220

[45] Date of Patent: Apr. 2, 1996

[54] PREPARATION OF α-TOCOPHEROL

[75] Inventors: Yeong J. Kuo; Gary W. Hartley; Bruce L. Gustafson; David J. Allen, all of Kingsport, Tenn.

[73] Assignee: Eastman Chemical Company, Kingsport, Tenn.

[21] Appl. No.: 516,088

[22] Filed: Aug. 17, 1995

[51] Int. Cl.$^6$ .................................................. C07D 311/76
[52] U.S. Cl. .................................................. 549/412
[58] Field of Search .................................................. 549/412

[56] References Cited

U.S. PATENT DOCUMENTS 3,819,657  6/1974  Baldwin et al. .......................... 549/412
4,239,691  12/1980  Nelan et al. ............................. 549/412

OTHER PUBLICATIONS

Chemical Abstract 112:139622—Abstract of EP 338,429 A2 (δ).
Chemical Abstract 106:50511—Abstract of JP 60–237,085 (δ).
Chemical Abstract 105:191442—Abstract of EP 1,784,000 A1 (δ).

Brunsuer, S., Emmet, P. H. and Teller, E., J. Am. Chem. Soc., 60, 309–16 @(1938).

Primary Examiner—Johann Richter
Assistant Examiner—Laura L. Stockton
Attorney, Agent, or Firm—J. Frederick Thomsen; Harry J. Gwinnell

[57] ABSTRACT

Disclosed is an improved process for the preparation of alpha-tocopherol by the hydroxymethylation followed by the hydrogenation of non-α-tocopherols comprising β-, γ-, and δ-tocopherols using a particular palladium on alumina catalyst wherein (1) the dispersion and depth of deposition of the palladium metal are within certain ranges, and (2) the alumina is of a particular crystalline phase.

5 Claims, No Drawings

PREPARATION OF α-TOCOPHEROL

This invention pertains to an improved process for the preparation of α-tocopherol by the hydroxymethylation followed by the hydrogenation of non-α-tocopherols comprising β-, γ-, and δ-tocopherols. More specifically, the present invention pertains to an improved process for the hydroxymethylation followed by the hydrogenation of the mixed tocopherols in the presence of certain, supported palladium catalysts which improve significantly the hydrogenation activity in the process.

Vitamin E consists of a mixture of α-, β-, γ-, and δ-tocopherols having the general formula:

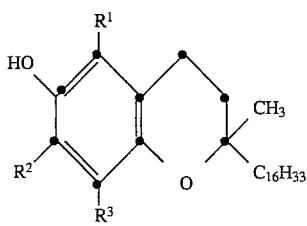

wherein
α=$R^1$=$R^2$=$R^3$=$CH_3$;
β=$R^1$=$R^3$=$CH_3$, $R^2$=H;
γ=$R^1$=H, $R^2$=$R^3$=$CH_3$; and
δ=$R^1$=$R^2$=H, $R^3$=$CH_3$.

It is known that non-α-tocopherols can be converted to α-tocopherol, the most potent form of Vitamin E, by various processes. For example, EP 338,429 A2 (C.A. 112:139622) discloses converting mixed tocopherols to α-tocopherol using paraformaldehyde in methanol containing a palladium on carbon catalyst and trimethyl phosphate under hydrogen. JP 60-237,085 (C.A. 106:50511) discloses a process for manufacturing α-tocopherol by treating mixed tocopherols with paraformaldehyde, an alkali metal bisulfate or aromatic sulfonic acid, a palladium on carbon catalyst, and hydrogen. EP 1,784,000 A1 (C.A. 105:191442) describes the conversion of non-α-tocopherols to the α-form using paraformaldehyde, zinc dust, zinc chloride, propionic acid, palladium on carbon catalyst, and hydrogen. U.S. Pat. No. 4,239,691 discloses the manufacture of α-tocopherol from non-α-tocopherols using paraformaldehyde, methanol, an acidic ion exchange resin, palladium on carbon catalyst, and hydrogen. U.S. Pat. No. 3,829,657 discloses the conversion of non-α-tocopherols to α-tocopherol using formaldehyde in the presence of orthophosphoric acid and catalytic hydrogenation.

The present invention provides a process for the conversion of non-α-tocopherols to α-tocopherol wherein a mixture of α-, β-, γ-, and δ-tocopherols is contacted, at elevated temperatures and pressures, with formaldehyde and hydrogen in the presence of a non-reactive (inert) solvent and a particular palladium catalyst. During the process, hydroxymethylation occurs first, followed quickly by hydrogenolysis of the benzylic residue to effect methylation of the aromatic ring of the non-α-tocopherols. The hydroxymethylation reaction occurs rapidly under reaction conditions, and the benzylic alcohol will proceed to a by-product if not hydrogenated quickly enough. If the rate of hydrogenation can be increased, the rate of hydroxymethylation can be increased without an increase in by-product formation. The hydrogenation rate enhancement also allows for adequate hydrogenolysis of the hydoxymethylated non-α-tocopherol to occur at lower temperatures.

We have discovered that excellent rates may be achieved by the use of palladium on alumina catalysts wherein (1) the dispersion and depth of deposition of the palladium metal are within certain ranges, and (2) the alumina is of a particular crystalline phase. We also have found that the described herein is less selective toward hydrogenation of formaldehyde; therefore less formaldehyde can be used in the present invention to obtain an equivalent conversion. The process provided by our invention therefore provides a means for the preparation of α-tocopherol which comprises contacting a mixture of α-, β-, γ-, and δ-tocopherols, at elevated temperatures and pressures, with formaldehyde and hydrogen in the presence of a non-reactive (inert) diluent and a palladium on alumina catalyst; wherein (1) palladium comprises about 0.1 to 5.0 weight percent of the catalyst;
(2) the palladium dispersion is at least 25 percent;
(3) at least 90 weight percent of the palladium is located on the alumina at a depth less than 250 microns from the surface of the alumina; and
(4) the crystalline phase of the alumina is gamma, eta or a mixture thereof.

According to this invention, the process is carried out at a temperature of about 150° to 400° C., preferably at 175° to 300° C. since decomposition of the tocopherols may occur at temperatures above 300° C. The elevated pressure range at which the process is operated may be from about 70 to 277 bars absolute (1016–4019 pounds per square inch absolute, psia) with the range of 87 to 173 bars absolute (1262–2510 psia) being preferred.

In operation of the present invention, a mixture of α-, β-, γ-, and δ-tocopherols are contacted with formaldehyde or a source of formaldehyde in the presence of a non-reactive or inert diluent or mixture of diluents, preferably a lower, primary alkanol such as methanol, ethanol, propanol, and butanol. The mixed tocopherols used in the process typically are present in a tocopherol concentrate comprising about 20 to 60 weight percent tocopherols and about 80 to 40 weight percent other organic, vegetable oil constituents. Non-α-tocopherols typically comprise about 60 to 80 weight percent of the total tocopherol content of the tocopherol concentrate.

Paraformaldehyde may be used as the formaldehyde source in batch operation but, in continuous operation of the process, the use of a solution of formaldehyde in a solvent such as a lower alkanol, e.g., methanol and butanol, is preferred. Alternatively, formaldehyde sources such as dimethoxymethane or trioxane may be used. The formaldehyde weight percentage in the solution may be in the range of about 10 to 55%, with the range of about 20 to 40% being preferred. The formaldehyde solution to tocopherol concentrate volumetric feed ratio may be in the range of about 1:1 to 25:1, with a range of about 2:1 to 14:1 being preferred. The formaldehyde:non-α-tocopherol mole ratio normally is maintained at least 10:1, typically in the range of about 15:1 to 70:1.

The catalyst used in the present invention is palladium deposited on an alumina support wherein the palladium comprises about 0.1 to 5.0, preferably 0.5 to 2.0, weight percent based on the total weight of the catalyst. The dispersion of the palladium on and in the alumina support typically is measured by titration of the surface of the catalyst with carbon monoxide gas and measuring the amount of carbon monoxide adsorbed on the palladium surface. Normally, it is assumed that each surface metal atom will adsorb one molecule of carbon monoxide and thus, the percent of metal exposed may be determined. This percentage is known as the dispersion. See Myasaki, J. Catal., 65, 84 (1980) and "Structure of Metallic Catalysts"

by J. R. Anderson, Academic Press, 1975, page 360. The catalysts which are advantageously used in accordance with the present invention have a dispersion percentage of at least 25 percent, preferably at least 30 percent (as determined by carbon monoxide adsorption as described herein). The maximum dispersion value generally is about 60 percent.

Another characteristic of the palladium catalyst used in the present invention is that most of the palladium is located on or near the surface of the alumina support. Accordingly, at least 90 weight percent of the palladium is located no deeper than about 500 microns, preferably less than 250 microns, from the external surface of the alumina support. As is well-known in the art, depth of impregnation can be determined either visually using optical microscopy or by a line scan technique in a scanning electron microscope with a palladium sensitive detector. See, for example, the above-cited "Structure of Metallic Catalysts".

Yet another important characteristic of the catalysts is the crystalline phase of the alumina support which is selected from the alpha, theta, delta, gamma, or eta phases, or a mixture of such crystalline phases. Alumina of gamma or eta crystalline phases or mixture of such alumina is preferred, with gamma alumina being especially preferred.

The nitrogen BET surface area of the palladium on alumina catalysts used in the process of our invention is in the range of about 100 to 300 square meters per gram ($m^2/g$) with the range of about 150 to 250 $m^2/g$ being preferred. It is well known in the art that BET surface area is a function of crystalline phase and calcination history and should be as high as possible while maintaining the appropriate oxide phase.

Catalysts having the characteristics described hereinabove may be prepared according to conventional impregnation or deposition techniques using procedures well known to those skilled in the art. The catalyst may be used in the hydrogenation process in the form of pellets, spheres, cylindrical or non-cylindrical extrudates, and the like. The particular form is not critical so long as the catalyst form (i) does not lead to excessive channeling of the liquid feed through the reactor, e.g., in continuous operation using a fixed bed of catalyst through which the reactant is passed; (ii) provides superior liquid hold up in the catalytic system; and (iii) increases the surface area to volume ratio over conventional palladium on alumina catalysts. The surface area:volume ratio of the catalyst normally is at least 1000 square meters per cubic meter ($m^2/m^3$), preferably greater than 1500 $m^2/m^3$ and, most preferably, greater than 2000 $m^2/m^3$. The upper limit on the surface area:volume ratio is about 4000 $m^2/m^3$.

The process of the invention may be carried out in a batch, semi-continuous or continuous mode using conventional chemical processing techniques. The preferred mode of operation is a continuous process wherein the mixed tocopherols are passed over and through one or more fixed beds of catalyst in a "trickle bed" manner. Typically, a major portion of the reaction product comprising tocopherol concentrate enriched in α-tocopherol is recycled to the feed port of the reactor along with unreacted feed material, i.e., untreated tocopherol concentrate. The process may be operated in either an adiabatic or isothermal fashion. In trickle bed operation, the liquid hourly space velocity (LHSV; unit volume reactant fed per hour per unit volume catalyst) of the tocopherol concentrate feed may be in the range of about 25 to 600 mL/L-hour with a preferred range of about 50 to 300 mL/L-hour; the liquid hourly space velocity of the formaldehyde/solvent, preferably formaldehyde/methanol, feed may be in the range of about 100 to 2500 mL/L-hour with a preferred range of about 200 to 1300 mL/L-hour. The LHSV for the total liquid flow (reactant plus solvent plus recycle) may be in the range of about 1 to 30 L/L-h. Hydrogen is fed to the reactor in excess of the stoichiometric quantity and normally is purged from the system. The rate of hydrogen purge is dependent on the temperature and pressure at which the process is operated.

Our novel process is further illustrated by the following examples. The palladium on alumina catalysts employed in the examples are described in Table I wherein % Pd is the nominal weight percent palladium present on the catalyst, BET SA is the BET surface area of the catalyst in $m^2/g$, Pd Disp. is the percent of the palladium which is exposed, Impreg. Depth is the maximum depth in microns at which at least 90 weight percent the palladium is impregnated on and in the support, and Phase is the crystalline phase of the alumina support.

TABLE I

| Catalyst | % Pd | BET SA | Pd Disp. | Impreg. Depth | Phase |
| --- | --- | --- | --- | --- | --- |
| A | 1 | 202 | 39 | 200 | Gamma |
| B | 1 | 190 | 38 | 200 | Gamma |
| C | 2 | 180 | 50 | 250 | Gamma |
| D | 1 | 115 | 40 | 100 | Theta |
| E | 1 | 103 | 28 | 500 | Gamma |
| F | 1 | 112 | 48 | >1000 | Theta |

EXAMPLES 1–3 AND COMPARATIVE EXAMPLES 1–5

Each hydroxymethylation/hydrogenation experiment was conducted in a 1-liter autoclave equipped with a catalyst basket, a stir fin, a thermocouple, a pressure gauge, gas inlet and outlet tubes, and a liquid sampling tube and means for heating and cooling the autoclave. In each example, a tocopherol concentrate (50 g) which contains 12% α-, 3% β-, 20% γ-, and 8% δ-tocopherol methanol (250 g), and one of the catalysts (10 g) described in Table I were charged to the autoclave. The catalyst was kept inside the basket which was immersed in the reaction mixture. The autoclave was first pressurized to 14.8 bars absolute (215 psia) with hydrogen at room temperature. Stirring was started and the autoclave was heated to 235° C. Formaldehyde/methanol (60:40 parts by weight) solution (50 g) then was pumped into the autoclave in 2 hours. The autoclave was pressurized to 159.6 bars absolute (2315 psia) with hydrogen at 235° C. which was the beginning of the 20-hour reaction time employed in each experiment. After the 20-hour reaction period, the autoclave was cooled and vented carefully to minimize the loss of the contents. The liquid product was analyzed by both gas chromatography and high pressure liquid chromatography. The results are summarized in Table II wherein C-1 through C-6 designate the comparative examples, and Conversion is the mole percent of non-α-tocopherols in the reactant which were converted to α-tocopherol.

EXAMPLES 4–5 AND COMPARATIVE EXAMPLES 6

Using the procedure employed in Examples 1–3 and Comparative Examples 1–5, a tocopherol concentrate (60 g) containing 12% α-, 3% β-, 20% γ-, and 8% δ-tocopherol, methanol (840 g), and one of the catalysts (30–35 g) described in Table I were charged to a 1.8-liter autoclave equipped similarly to the autoclave used in the preceding examples. The catalyst was kept inside the basket which was immersed in the reaction mixture. The autoclave was first pressurized to 56.2 bars absolute (815 psia) with hydrogen at room temperature. Stirring was started and the autoclave was heated to 235° C. Formaldehyde/methanol (60:40 parts by weight) solution (160 g) then was pumped into the autoclave in 1 hour. The autoclave was pressurized to 242.3 bars absolute (3515 psia) with hydrogen at 235° C. which was the beginning of the 40-hour reaction time employed in each experiment. Upon completion of the reaction period, the autoclave was cooled and vented carefully to minimize the loss of the contents. The liquid product was analyzed by both gas chromatography and high pressure liquid chromatography. The results are summarized in Table II.

TABLE II

| Example | Catalyst | Conversion |
| --- | --- | --- |
| 1 | A | 76.60 |
| 2 | B | 74.00 |
| 3 | B | 78.00 |
| C-1 | D | 51.70 |
| C-2 | D | 52.40 |
| C-3 | E | 53.00 |
| C-4 | E | 55.40 |
| C-5 | F | 33.80 |
| 4 | B | 70.50 |
| 5 | C | 67.15 |
| C-6 | E | 54.60 |

The conversions reported in Table II demonstrate the advantages provided by the present invention utilizing Catalyst A, B or C which have the unique combination of characteristics specified above.

EXAMPLES 6–14 AND COMPARATIVE EXAMPLES 7–11

All experiments were performed in a trickle bed reactor system comprising a 1.83 meter (6 feet) section of 316 stainless steel pipe having an interior diameter of 2.5 cm (1 inch) and equipped with means for liquid recycle. The catalyst (600–800 mL) was held in place within the reactor by 100 mL of 6 mm borosilicate glass beads located above and below the catalyst bed. The temperatures at various points within the catalyst bed were measured by 10 thermocouples which extended through the reactor wall and approximately 3.2 mm into the catalyst. The temperature reported in each example is the average of these 10 readings. Typical temperature gradients through the bed were less than 5° C.

The general procedure used in each experiment comprised purging the system with hydrogen and pumping tocopherol concentrate (30–200 mL/hour), having a similar composition as that in Examples 1–5, through the reactor system at 75°–100° C. and 104.4 bars absolute (1515 psia) with a 15 L/hour liquid recycle. The temperature slowly was increased to the desired reaction temperature. The reaction was commenced when formaldehyde/methanol feed solution (30:70 parts by weight, 150–900 mL/hr) was pumped into the reactor. Hydrogen was purged from the reactor system at a rate of about 8 to 10 L/minute. Operating data were recorded when a steady state of operation was achieved, typically 2 to 3 hours from the commencement of the reaction. The liquid products were analyzed by high pressure liquid chromatography. The results are summarized in Table III wherein Temp is the average reaction temperature in °C., Toc. LHSV is mL tocopherol concentrate per L catalyst-hour, Ald. LHSV is mL formaldehyde/methanol solution per L catalyst-hour, and Conv. is the mole percent non-α-tocopherols in the reactant converted to α-tocopherol.

TABLE III

| Example | Catalyst | Temp | Toc. LHSV | Ald. LHSV | Conv. |
| --- | --- | --- | --- | --- | --- |
| 6 | B | 200 | 62 | 355 | 76 |
| 7 | C | 200 | 60 | 280 | 53 |
| C-7 | E | 200 | 62 | 367 | 51 |
| 8 | B | 200 | 93 | 400 | 68 |
| 9 | C | 200 | 87 | 479 | 63 |
| C-8 | E | 200 | 93 | 391 | 50 |
| 10 | B | 235 | 132 | 650 | 72 |
| 11 | C | 235 | 140 | 670 | 52 |
| C-9 | E | 235 | 149 | 693 | 44 |
| 12 | B | 235 | 210 | 913 | 64 |
| 13 | C | 235 | 200 | 888 | 56 |
| C-10 | E | 235 | 200 | 879 | 43 |
| 14 | B | 235 | 70 | 233 | 75 |
| C-11 | E | 235 | 56 | 676 | 68 |

The conversions reported in Table III demonstrate again the advantages provided by the present invention utilizing Catalysts B and C which have a unique combination of characteristics and produce results significantly superior to those provided by Catalyst E. The data presented in Table III also show that the use of Catalyst B permits the use of less formaldehyde reactant to achieve higher conversion (compare Examples and C-11). Examples 6 and C-11 illustrate that by utilizing Catalyst B, higher conversion can be achieved while using both lower temperatures and lower formaldehyde usage.

The invention has been described in detail with particular reference to preferred embodiments thereof, but it will be understood that variations and modifications can be effected within the spirit and scope of the invention.

We claim:

1. A process for the preparation of α-tocopherol which comprises contacting a mixture of α-, β-, γ-, and δ-tocopherols, at elevated temperature and pressure, with formaldehyde and hydrogen in the presence of a non-reactive diluent and a palladium on alumina catalyst, wherein (1) palladium comprises about 0.1 to 5.0 weight percent of the catalyst;

(2) the palladium dispersion is at least 25 percent;

(3) at least 90 weight percent of the palladium is located on the alumina at a depth less than 250 microns from the surface of the alumina; and (4) the crystalline phase of the alumina is gamma, eta or a mixture thereof.

2. The process according to claim 1 wherein the elevated temperature and pressure are in the range of about 175° to 300° C. and about 87 to 173 bars absolute.

3. The process according to claim 2 wherein the catalyst has a nitrogen BET surface area of about 150 to 250 square meters per gram and the surface area to volume ratio is greater than 1500 square meters per cubic meter.

4. The process according to claim 1 wherein a mixture of α-, β-, γ-, and δ-tocopherols is contacted at a temperature of about 175° to 300° C. and a pressure of about 87 to 173 bars absolute with formaldehyde and hydrogen in the presence of a lower, primary alkanol diluent and a palladium on alumina catalyst, wherein (1) palladium comprises about 0.5 to 2.0 weight percent of the catalyst;

(2) the palladium dispersion is at least 30 percent;

(3) at least 90 weight percent of the palladium is located on the alumina at a depth less than 250 microns from the surface of the alumina; and (4) the crystalline phase of the alumina is gamma.

5. The process according to claim 4 wherein the BET surface area of the catalyst is in the range of 150 to 250 square meters per gram and the surface area to volume ratio of the catalyst is greater than 2000 square meters per cubic meter.

* * * * *